(12) United States Patent
Schorzman et al.

(10) Patent No.: US 7,759,408 B2
(45) Date of Patent: Jul. 20, 2010

(54) SILICON-CONTAINING MONOMERS END-CAPPED WITH POLYMERIZABLE CATIONIC HYDROPHILIC GROUPS

(75) Inventors: Derek Schorzman, Pittsford, NY (US); Joseph C. Salamone, Boca Raton, FL (US); Jay Kunzler, Canandaigua, NY (US); Jeffrey G. Linhardt, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 1169 days.

(21) Appl. No.: 11/341,209

(22) Filed: Jan. 27, 2006

(65) Prior Publication Data

US 2007/0142584 A1 Jun. 21, 2007

Related U.S. Application Data

(60) Provisional application No. 60/752,663, filed on Dec. 21, 2005.

(51) Int. Cl.
*G02B 1/04* (2006.01)
*C08F 290/06* (2006.01)

(52) U.S. Cl. ............... 523/107; 523/106; 526/258; 526/260; 526/266; 526/279; 526/303.1; 526/310; 526/312; 526/317.1; 526/321; 526/322; 528/25; 528/28; 528/38; 623/4.1; 623/5.11; 623/6.11

(58) Field of Classification Search .............. None
See application file for complete search history.

(56) References Cited

U.S. PATENT DOCUMENTS

| | | | |
|---|---|---|---|
| 3,808,179 A | 4/1974 | Gaylord | |
| 3,884,886 A * | 5/1975 | Plueddemann | ............... 526/258 |
| 4,005,024 A | 1/1977 | Rodriguez et al. | |
| 4,006,176 A | 2/1977 | Heckert et al. | |
| 4,153,641 A | 5/1979 | Deichert et al. | |
| 4,185,087 A | 1/1980 | Morlino | |
| 4,189,546 A | 2/1980 | Deichert et al. | |
| 4,259,467 A | 3/1981 | Keogh et al. | |
| 4,260,725 A | 4/1981 | Keogh et al. | |
| 4,388,229 A | 6/1983 | Fu | |
| 4,418,165 A | 11/1983 | Polmanteer et al. | |
| 4,472,327 A | 9/1984 | Neefe | |
| 4,495,361 A | 1/1985 | Friends et al. | |
| 4,533,714 A | 8/1985 | Sebag et al. | |
| 4,633,003 A | 12/1986 | Falcetta et al. | |
| 4,640,941 A | 2/1987 | Park et al. | |
| 4,686,267 A | 8/1987 | Ellis et al. | |
| 4,745,142 A | 5/1988 | Ohwaki et al. | |
| 4,833,225 A | 5/1989 | Schaefer et al. | |
| 4,871,530 A | 10/1989 | Grollier et al. | |
| 4,891,166 A | 1/1990 | Schaefer et al. | |
| 4,910,277 A | 3/1990 | Bambury et al. | |
| 5,006,622 A | 4/1991 | Kunzler et al. | |
| 5,013,459 A | 5/1991 | Gettings et al. | |
| 5,034,461 A | 7/1991 | Lai et al. | |
| 5,039,458 A | 8/1991 | Braatz et al. | |
| 5,070,170 A | 12/1991 | Robertson et al. | |
| 5,070,215 A | 12/1991 | Bambury et al. | |
| 5,128,408 A | 7/1992 | Tanaka et al. | |
| 5,137,448 A | 8/1992 | Dougherty et al. | |
| 5,246,607 A | 9/1993 | Schaefer et al. | |
| 5,260,000 A | 11/1993 | Nandu et al. | |
| 5,321,108 A | 6/1994 | Kunzler et al. | |
| 5,340,583 A | 8/1994 | Dziabo et al. | |
| 5,358,688 A | 10/1994 | Robertson | |
| 5,358,995 A | 10/1994 | Lai et al. | |
| 5,359,104 A | 10/1994 | Higgs et al. | |
| 5,387,105 A | 2/1995 | Dougherty et al. | |
| 5,387,662 A | 2/1995 | Kunzler et al. | |
| 5,393,330 A | 2/1995 | Chen et al. | |
| 5,420,324 A | 5/1995 | Lai et al. | |
| 5,451,617 A | 9/1995 | Lai et al. | |
| 5,451,651 A | 9/1995 | Lai | |

(Continued)

FOREIGN PATENT DOCUMENTS

EP 0 017 121 4/1983

(Continued)

OTHER PUBLICATIONS

Abstract for the article entitled, "Influence of the Chemical Structure of N-alkyl-N,N-dimethyl-3-(siloxanyl)propylammonium Bromides on the Adsorption at the Mercury/Electrolyte Interface" authored by Retter et al. and published in the Journal of Colloid and Interface Science (1993), 156(1), p. 85-89.*

(Continued)

*Primary Examiner*—Marc S Zimmer
(74) *Attorney, Agent, or Firm*—Glenn D. Smith; M. Carmen & Associates, PLLC

(57) ABSTRACT

The present invention relates to polymeric compositions useful in the manufacture of biocompatible medical devices. More particularly, the present invention relates to certain cationic monomers capable of polymerization to form polymeric compositions having desirable physical characteristics useful in the manufacture of ophthalmic devices. Such properties include the ability to extract the polymerized medical devices with water. This avoids the use of organic solvents as is typical in the art. The polymer compositions comprise polymerized silicon-containing monomers end-capped with polymerizable cationic hydrophilic groups.

37 Claims, No Drawings

U.S. PATENT DOCUMENTS

| | | | |
|---|---|---|---|
| 5,496,871 A | 3/1996 | Lai | |
| 5,515,117 A | 5/1996 | Dziabo et al. | |
| 5,539,016 A | 7/1996 | Kunzler et al. | |
| 5,594,085 A | 1/1997 | Lai | |
| 5,610,252 A | 3/1997 | Bambury et al. | |
| 5,639,908 A | 6/1997 | Lai | |
| 5,648,515 A | 7/1997 | Lai | |
| 5,707,434 A | 1/1998 | Halloran et al. | |
| 5,710,302 A | 1/1998 | Kunzler et al. | |
| 5,714,557 A | 2/1998 | Kunzler et al. | |
| 5,725,736 A | 3/1998 | Schroeder et al. | |
| 5,776,999 A | 7/1998 | Nicolson et al. | |
| 5,807,956 A | 9/1998 | Czech | |
| 5,830,546 A | 11/1998 | Ehret et al. | |
| 5,844,026 A | 12/1998 | Galbo et al. | |
| 5,908,906 A | 6/1999 | Kunzler et al. | |
| 5,962,548 A | 10/1999 | Vanderlaan et al. | |
| 5,994,488 A | 11/1999 | Yokota | |
| 6,013,711 A | 1/2000 | Lewis et al. | |
| 6,022,836 A | 2/2000 | Dubief et al. | |
| 6,063,888 A | 5/2000 | Yamaguchi et al. | |
| 6,068,929 A | 5/2000 | Dauth et al. | |
| 6,132,705 A | 10/2000 | Schelmann et al. | |
| 6,166,236 A | 12/2000 | Bambury et al. | |
| 6,242,554 B1 | 6/2001 | Busch et al. | |
| 6,248,803 B1 | 6/2001 | Nakanishi et al. | |
| 6,482,969 B1 | 11/2002 | Helmrick et al. | |
| 6,534,184 B2 | 3/2003 | Knasiak et al. | |
| 6,607,717 B1 | 8/2003 | Johnson et al. | |
| 6,613,755 B2 | 9/2003 | Peterson et al. | |
| 6,630,132 B2 | 10/2003 | Fender et al. | |
| 6,649,722 B2 | 11/2003 | Rosenzweig et al. | |
| 6,706,680 B2 | 3/2004 | Fender et al. | |
| 6,730,767 B2 | 5/2004 | Salamone et al. | |
| 6,787,603 B2 | 9/2004 | Johnson et al. | |
| 6,815,074 B2 | 11/2004 | Aguado et al. | |
| 6,822,016 B2 | 11/2004 | McCabe et al. | |
| 6,849,671 B2 | 2/2005 | Steffen et al. | |
| 6,849,755 B2 | 2/2005 | Ozai et al. | |
| 6,852,793 B2 | 2/2005 | Salamone et al. | |
| 6,893,595 B1 | 5/2005 | Muir et al. | |
| 6,951,894 B1 | 10/2005 | Nicolson et al. | |
| 7,468,397 B2 | 12/2008 | Schorzman | |
| 7,528,208 B2 | 5/2009 | Schorzman et al. | |
| 7,557,231 B2 | 7/2009 | Schorzman et al. | |
| 7,601,766 B2 | 10/2009 | Schorzman et al. | |
| 7,622,512 B2 | 11/2009 | Schorzman et al. | |
| 2003/0108494 A1* | 6/2003 | Fender et al. | 424/59 |
| 2004/0029981 A1 | 2/2004 | Herzig et al. | |
| 2005/0008613 A1 | 1/2005 | Peterson et al. | |

FOREIGN PATENT DOCUMENTS

| | | | |
|---|---|---|---|
| EP | 0 396 364 | | 6/1997 |
| EP | 0 837 103 | | 4/1998 |
| EP | 0 837 104 | | 4/1998 |
| JP | 9183813 | | 7/1997 |
| WO | WO 2007/070653 | * | 6/2007 |

OTHER PUBLICATIONS

International Search Report (PCTISA/210) and Written Opinion (PCT/ISA/237) mailed on Jun. 28, 2007.
William J. Benjamin, et al., The Oxygen Permeability of Reference Materials, Optom Vis Sci 7 (12s): 95 (1997).
Benjamin, William J., Oxygen Permeability (Dk) of Thirty-Seven Rigid Contact Lens Materials, Optometry and Vision Science, vol. 79, No. 2, Feb. 2002, pp. 103-111.
U.S. Appl. No. 11/403,393, filed Apr. 13, 2006, Schorzman et al.
U.S. Appl. No. 11/480,111, filed Jun. 30, 2006, Schorzman et al.
U.S. Appl. No. 11/480,170, filed Jun. 30, 2006, Schorzman et al.
U.S. Appl. No. 11/611,508, filed Dec. 15, 2006, Schorzman et al.
U.S. Appl. No. 11/611,512, filed Dec. 15, 2006, Schorzman et al.
U.S. Appl. No. 11/619,211, filed Jan. 3, 2007, Schorzman et al.
U.S. Appl. No. 11/830,885, filed Jul. 31, 2007, Schorzman et al.
U.S. Appl. No. 11/837,049, filed Aug. 10, 2007, Kunzler et al.
U.S. Appl. No. 11/840,650, filed Aug. 17, 2007, Salamone et al.
U.S. Appl. No. 12/018,910, filed Jun. 24, 2008, Stanbro et al.
U.S. Appl. No. 12/313,253, filed Nov. 18, 2008, Schorzman.
U.S. Appl. No. 12/459,778, filed Jul. 8, 2009, Kunzler et al.
U.S. Appl. No. 12/459,779, filed Jul. 8, 2009, Kunzler et al.

* cited by examiner

SILICON-CONTAINING MONOMERS END-CAPPED WITH POLYMERIZABLE CATIONIC HYDROPHILIC GROUPS

CROSS-REFERENCE TO RELATED APPLICATIONS

This application claims the benefit under 35 USC 119(e) of Provisional Patent Application No. 60/752,663 filed Dec. 21, 2005.

FIELD

The present invention relates to polymeric compositions useful in the manufacture of biocompatible medical devices. More particularly, the present invention relates to certain cationic monomers capable of polymerization to form polymeric compositions having desirable physical characteristics useful in the manufacture of ophthalmic devices. Such properties include the ability to extract the polymerized medical devices with water. This avoids the use of organic solvents as is typical in the art. The polymer compositions comprise polymerized silicon containing monomers end-capped with ethylenically unsaturated cationic hydrophilic groups.

BACKGROUND AND SUMMARY

Various articles, including biomedical devices, are formed of organosilicon-containing materials. One class of organosilicon materials useful for biomedical devices, such as soft contact lenses, is silicon-containing hydrogel materials. A hydrogel is a hydrated, cross linked polymeric system that contains water in an equilibrium state. Hydrogel contact lenses offer relatively high oxygen permeability as well as desirable biocompatibility and comfort. The inclusion of a silicon-containing material in the hydrogel formulation generally provides higher oxygen permeability since silicon based materials have higher oxygen permeability than water.

Another class of organosilicon materials is rigid, gas permeable materials used for hard contact lenses. Such materials are generally formed of silicon or fluorosilicon copolymers. These materials are oxygen permeable, and more rigid than the materials used for soft contact lenses. Organosilicon-containing materials useful for biomedical devices, including contact lenses, are disclosed in the following U.S. patents: U.S. Pat. No. 4,686,267 (Ellis et al.); U.S. Pat. No. 5,034,461 (Lai et al.); and U.S. Pat. No. 5,070,215 (Bambury et al.).

In addition, traditional siloxane-type monomers are hydrophobic and lenses made with them frequently require additional treatment to provide a hydrophilic surface. Although not wishing to be bound by a particular theory, the inventors believe that providing a charged siloxane-type monomer such as the quaternary siloxane-type monomers disclosed herein results in a hydrophilic siloxane-type monomer. It is believed that the hydrophilic quaternary groups interact with the electronegative portion of the polar water molecule.

Soft contact lens materials are made by polymerizing and crosslinking hydrophilic monomers such as 2-hydroxyethylmethyacrylate, N-vinyl-2-pyrrolidone, and combinations thereof. The polymers produced by polymerizing these hydrophilic monomers exhibit significant hydrophilic character themselves and are capable of absorbing a significant amount of water in their polymeric matrices. Due to their ability to absorb water, these polymers are often referred to as "hydrogels". These hydrogels are optically clear and, due to their high levels of water of hydration, are particularly useful materials for making soft contact lenses. Siloxane-type monomers are well known to be poorly soluble in water as well as hydrophilic solvents and monomers and are therefore difficult to copolymerize and process using standard hydrogel techniques. Therefore, there is a need for new siloxane-type monomers that have improved solubility in the materials, specifically the diluents, used to make hydrogel lenses. Further there is a need for monomers that result in a polymerized medical device that is extractable in water instead of the organic solvents used in the prior art.

The term "monomer" and like terms as used herein denote relatively low molecular weight compounds that are polymerizable by, for example, free radical polymerization, as well as higher molecular weight compounds also referred to as "prepolymers", "macromonomers", and related terms.

The term "(meth)" as used herein denotes an optional methyl substituent. Accordingly, terms such as "(meth)acrylate" denotes either methacrylate or acrylate, and "(meth) acrylic acid" denotes either methacrylic acid or acrylic acid.

The present invention provides novel cationic organosilicon-containing monomers which are useful in articles such as biomedical devices including contact lenses.

BRIEF DESCRIPTION OF THE DRAWINGS

None

DETAILED DESCRIPTION

In a first aspect, the invention relates to monomers of formula (I):

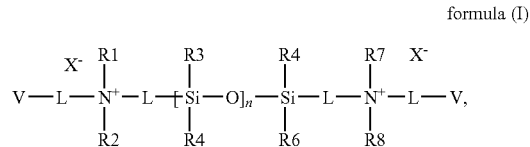

formula (I)

wherein L can be the same or different and is selected from the group consisting of urethanes, carbonates, carbamates, carboxyl ureidos, sulfonyls, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, a C5-C30 fluoroaryl group, or a hydroxyl substituted alkyl ether and combinations thereof.

$X^-$ is at least a single charged counter ion. Examples of single charge counter ions include the group consisting of $Cl^-$, $Br^-$, $I^-$, $CF_3CO_2^-$, $CH_3CO_2^-$, $HCO_3^-$, $CH_3SO_4^-$, p-toluenesulfonate, $HSO_4^-$, $H_2PO_4^-$, $NO_3^-$, and $CH_3CH(OH)CO_2^-$. Examples of dual charged counter ions would include $SO_4^{2-}$, $CO_3^{2-}$ and $HPO_4^{2-}$. Other charged counter ions would be obvious to one of ordinary skill in the art. It should be understood that a residual amount of counter ion may be present in the hydrated product. Therefore, the use of toxic counter ions is to be discouraged. Likewise, it should be understood that, for a singularly charged counter ion, the ratio of counter ion and quaternary siloxanyl will be 1:1. Counter ions of greater negative charge will result in differing ratios based upon the total charge of the counter ion.

n is an integer from 1 to about 300; $R_1$, $R_2$, $R_3$, $R_4$, $R_5$, $R_6$, $R_7$ and $R_8$ are each independently hydrogen, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocycloalkyl group, a substituted or unsubstituted C6-C30 heteroarylalkyl group, fluorine, a C5-C30 fluoroaryl group, or a hydroxyl group; X is independently a straight or branched C1-C30 alkyl group, a C1-C30 fluoroalkyl group, a substituted or unsubstituted C5-C30 arylalkyl group, an ether, polyether, sulfide, or amino-containing group and V is independently a polymerizable ethylenically unsaturated organic radical.

Representative examples of urethanes for use herein include, by way of example, a secondary amine linked to a carboxyl group which may also be linked to a further group such as an alkyl. Likewise the secondary amine may also be linked to a further group such as an alkyl.

Representative examples of carbonates for use herein include, by way of example, alkyl carbonates, aryl carbonates, and the like.

Representative examples of carbamates, for use herein include, by way of example, alkyl carbamates, aryl carbamates, and the like.

Representative examples of carboxyl ureidos, for use herein include, by way of example, alkyl carboxyl ureidos, aryl carboxyl ureidos, and the like.

Representative examples of sulfonyls for use herein include, by way of example, alkyl sulfonyls, aryl sulfonyls, and the like.

Representative examples of alkyl groups for use herein include, by way of example, a straight or branched hydrocarbon chain radical containing carbon and hydrogen atoms of from 1 to about 18 carbon atoms with or without unsaturation, to the rest of the molecule, e.g., methyl, ethyl, n-propyl, 1-methylethyl (isopropyl), n-butyl, n-pentyl, etc., and the like.

Representative examples of fluoroalkyl groups for use herein include, by way of example, a straight or branched alkyl group as defined above having one or more fluorine atoms attached to the carbon atom, e.g., —$CF_3$, —$CF_2CF_3$, —$CH_2CF_3$, —$CH_2CF_2H$, —$CF_2H$ and the like.

Representative examples of ester groups for use herein include, by way of example, a carboxylic acid ester having one to 20 carbon atoms and the like.

Representative examples of ether or polyether containing groups for use herein include, by way of example, an alkyl ether, cycloalkyl ether, cycloalkenyl ether, aryl ether, arylalkyl ether wherein the alkyl, cycloalkyl, cycloalkylalkyl, cycloalkenyl, aryl, and arylalkyl groups are defined above, e.g., alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —$R_8OR_9$, wherein $R_8$ is a bond, an alkyl, cycloalkyl or aryl group as defined above and $R_9$ is an alkyl, cycloalkyl or aryl group as defined above, e.g., —$CH_2CH_2OC_6H_5$ and —$CH_2CH_2OC_2H_5$, and the like.

Representative examples of amide groups for use herein include, by way of example, an amide of the general formula —$R_{10}C(O)NR_{11}R_{12}$ wherein $R_{10}$, $R_{11}$ and $R_{12}$ are independently C1-C30 hydrocarbons, e.g., $R_{10}$ can be alkylene groups, arylene groups, cycloalkylene groups and $R_{11}$ and $R_{12}$ can be alkyl groups, aryl groups, and cycloalkyl groups as defined herein and the like.

Representative examples of amine groups for use herein include, by way of example, an amine of the general formula —$R_{13}NR_{14}R_{15}$ wherein $R_{13}$ is a C2-C30 alkylene, arylene, or cycloalkylene and $R_{14}$ and $R_{15}$ are independently C1-C30 hydrocarbons such as, for example, alkyl groups, aryl groups, or cycloalkyl groups as defined herein, and the like.

Representative examples of an ureido group for use herein include, by way of example, an ureido group having one or more substituents or unsubstituted ureido. The ureido group preferably is an ureido group having 1 to 12 carbon atoms. Examples of the substituents include alkyl groups and aryl groups. Examples of the ureido group include 3-methylureido, 3,3-dimethylureido, and 3-phenylureido.

Representative examples of alkoxy groups for use herein include, by way of example, an alkyl group as defined above attached via oxygen linkage to the rest of the molecule, i.e., of the general formula —$OR_{20}$, wherein $R_{20}$ is an alkyl, cycloalkyl, cycloalkenyl, aryl or an arylalkyl as defined above, e.g., —$OCH_3$, —$OC_2H_5$, or —$OC_6H_5$, and the like.

Representative examples of cycloalkyl groups for use herein include, by way of example, a substituted or unsubstituted non-aromatic mono or multicyclic ring system of about 3 to about 18 carbon atoms such as, for example, cyclopropyl, cyclobutyl, cyclopentyl, cyclohexyl, perhydronapthhyl, adamantyl and norbornyl groups bridged cyclic group or spirobicyclic groups, e.g., spiro-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 18 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 18 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 25 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined above directly bonded to an alkyl group as defined above, e.g., —CH2C6H5, —C2H5C6H5 and the like, wherein the aryl group can optionally contain one or more heteroatoms, e.g., O and N, and the like.

Representative examples of fluoroaryl groups for use herein include, by way of example, an aryl group as defined above having one or more fluorine atoms attached to the aryl group.

Representative examples of heterocyclic ring groups for use herein include, by way of example, a substituted or unsubstituted stable 3 to about 15 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined above. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined above directly bonded to an alkyl group as defined above. The heteroarylalkyl radical may be attached to the main structure at any carbon atom from the alkyl group that results in the creation of a stable structure.

Representative examples of heterocyclo groups for use herein include, by way of example, a substituted or unsubstituted heterocylic ring radical as defined above. The heterocyclo ring radical may be attached to the main structure at any heteroatom or carbon atom that results in the creation of a stable structure.

Representative examples of heterocycloalkyl groups for use herein include, by way of example, a substituted or unsubstituted heterocylic ring radical as defined above directly bonded to an alkyl group as defined above. The heterocycloalkyl radical may be attached to the main structure at carbon atom in the alkyl group that results in the creation of a stable structure.

Representative examples of a "polymerizable ethylenically unsaturated organic radicals" include, by way of example, (meth)acrylate-containing radicals, (meth)acrylamide-containing radicals, vinylcarbonate-containing radicals, vinylcarbamate-containing radicals, styrene-containing radicals and the like. In one embodiment, a polymerizable ethylenically unsaturated organic radical can be represented by the general formula:

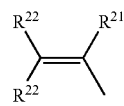

wherein R21 is hydrogen, fluorine or methyl; R22 is independently hydrogen, fluorine, an alkyl radical having 1 to 6 carbon atoms, or a —CO—Y—R24 radical wherein Y is —O—, —S— or —NH— and R24 is a divalent alkylene radical having 1 to about 10 carbon atoms.

The substituents in the 'substituted alkyl', 'substituted alkoxy', 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring' and 'substituted carboxylic acid derivative' may be the same or different and include one or more substituents such as hydrogen, hydroxy, halogen, carboxyl, cyano, nitro, oxo (═O), thio (═S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, substituted or unsubstituted guanidine, —COORx, —C(O)Rx, —C(S)Rx, —C(O)NRxRy, —C(O)ONRxRy, —NRxCONRyRz, —N(Rx)SORy, —N(Rx)SO2Ry, —(═N—N(Rx)Ry), —NRxC(O)ORy, —NRxRy, —NRxC(O)Ry—, —NRxC(S)Ry —NRxC(S)NRyRz, —SONRxRy—, —SO2NRxRy—, —ORx, —ORxC(O)NRyRz, —ORxC(O)ORy-, —OC(O)Rx, —OC(O)NRxRy, —RxNRyC(O)Rz, —RxORy, —RxC(O)ORy, —RxC(O)NRyRz, —RxC(O)Rx, —RxOC(O)Ry, —SRx, —SORx, —SO2Rx, —ONO2, wherein Rx, Ry and Rz in each of the above groups can be the same or different and can be a hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocycloalkyl ring' substituted or unsubstituted heteroarylalkyl, or a substituted or unsubstituted heterocyclic ring.

Preferred monomers of formula (I) are shown in formula (II) through formula (VI) below:

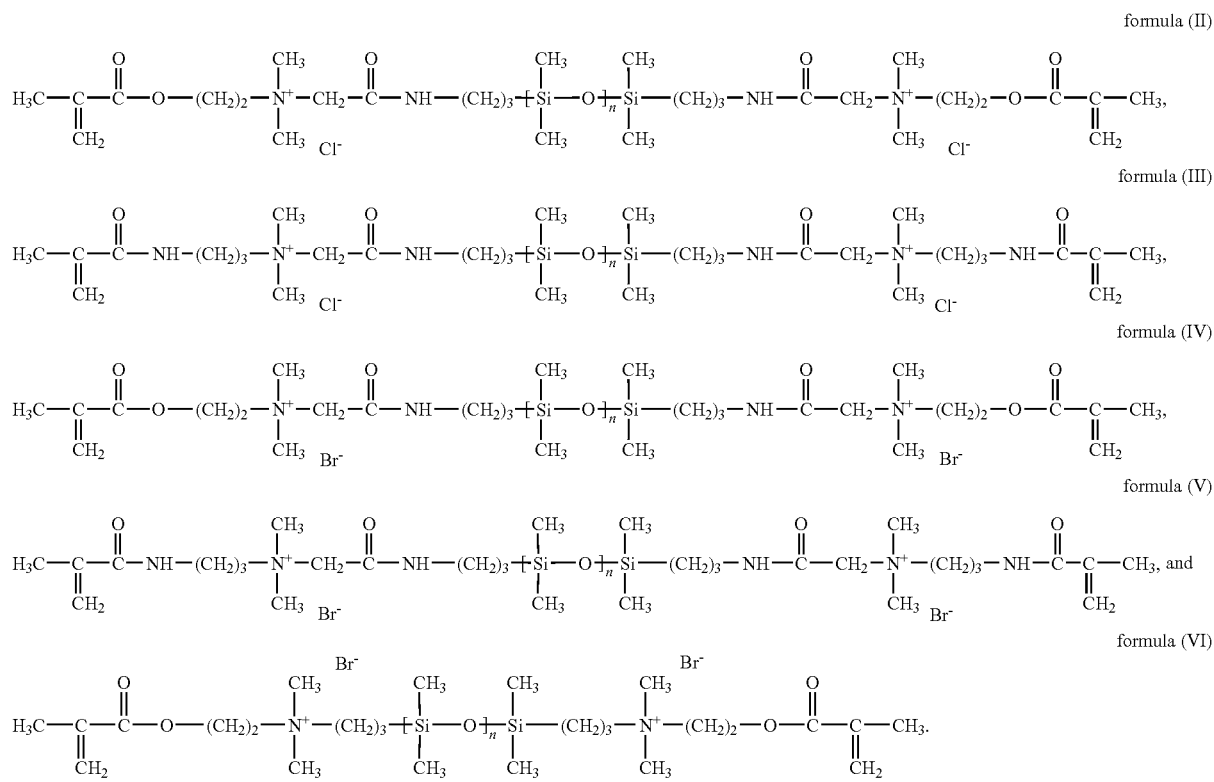
A schematic representation of a synthetic method for making the novel cationic silicon-containing monomers disclosed herein is provided below:
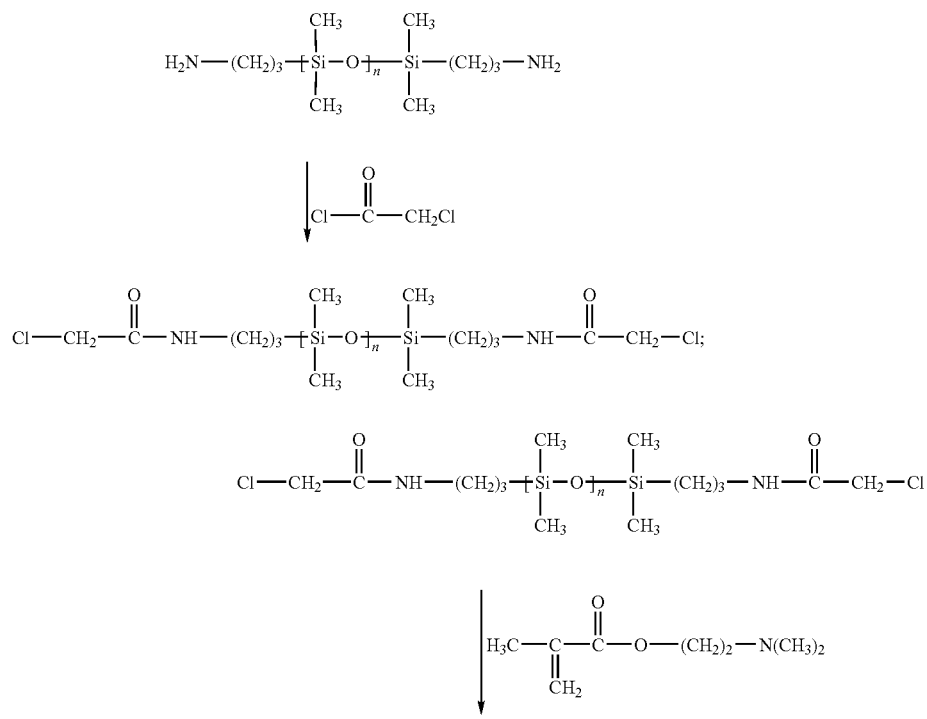

-continued

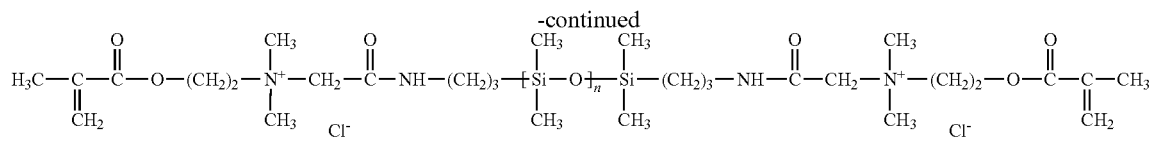

In a second aspect, the invention includes articles formed of device forming monomer mixes comprising the monomers of formula (I). According to preferred embodiments, the article is the polymerization product of a mixture comprising the aforementioned cationic monomer and at least a second monomer. Preferred articles are optically clear and useful as a contact lens.

Useful articles made with these materials may require hydrophobic, possibly silicon containing monomers. Preferred compositions have both hydrophilic and hydrophobic monomers. The invention is applicable to a wide variety of polymeric materials, either rigid or soft. Especially preferred polymeric materials are lenses including contact lenses, phakic and aphakic intraocular lenses and corneal implants although all polymeric materials including biomaterials are contemplated as being within the scope of this invention. Especially preferred are silicon containing hydrogels.

The present invention also provides medical devices such as heart valves and films, surgical devices, vessel substitutes, intrauterine devices, membranes, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, ophthalmic devices, and especially contact lenses.

Silicon containing hydrogels are prepared by polymerizing a mixture containing at least one silicon-containing monomer and at least one hydrophilic monomer. The silicon-containing monomer may function as a crosslinking agent (a crosslinker being defined as a monomer having multiple polymerizable functionalities) or a separate crosslinker may be employed.

An early example of a silicon-containing contact lens material is disclosed in U.S. Pat. No. 4,153,641 (Deichert et al assigned to Bausch & Lomb Incorporated). Lenses are made from poly(organosiloxane) monomers which are α, ω terminally bonded through a divalent hydrocarbon group to a polymerized activated unsaturated group. Various hydrophobic silicon-containing prepolymers such as 1,3-bis(methacryloxyalkyl) polysiloxanes were copolymerized with known hydrophilic monomers such as 2-hydroxyethyl methacrylate (HEMA).

U.S. Pat. No. 5,358,995 (Lai et al) describes a silicon containing hydrogel which is comprised of an acrylic ester-capped polysiloxane prepolymer, polymerized with a bulky polysiloxanylalkyl (meth)acrylate monomer, and at least one hydrophilic monomer. Lai et al is assigned to Bausch & Lomb Incorporated and the entire disclosure is incorporated herein by reference. The acrylic ester-capped polysiloxane prepolymer, commonly known as $M_2 D_x$ consists of two acrylic ester end groups and "x" number of repeating dimethylsiloxane units. The preferred bulky polysiloxanylalkyl (meth)acrylate monomers are TRIS-type (methacryloxypropyl tris(trimethylsiloxy)silane) with the hydrophilic monomers being either acrylic- or vinyl-containing.

Other examples of silicon-containing monomer mixtures which may be used with this invention include the following: vinyl carbonate and vinyl carbamate monomer mixtures as disclosed in U.S. Pat. Nos. 5,070,215 and 5,610,252 (Bambury et al); fluorosilicon monomer mixtures as disclosed in U.S. Pat. Nos. 5,321,108; 5,387,662 and 5,539,016 (Kunzler et al); fumarate monomer mixtures as disclosed in U.S. Pat. Nos. 5,374,662; 5,420,324 and 5,496,871 (Lai et al) and urethane monomer mixtures as disclosed in U.S. Pat. Nos. 5,451,651; 5,648,515; 5,639,908 and 5,594,085 (Lai et al), all of which are commonly assigned to assignee herein Bausch & Lomb Incorporated, and the entire disclosures of which are incorporated herein by reference.

Examples of non-silicon hydrophobic materials include alkyl acrylates and methacrylates.

The cationic silicon-containing monomers may be copolymerized with a wide variety of hydrophilic monomers to produce silicon hydrogel lenses. Suitable hydrophilic monomers include: unsaturated carboxylic acids, such as methacrylic and acrylic acids; acrylic substituted alcohols, such as 2-hydroxyethylmethacrylate and 2-hydroxyethylacrylate; vinyl lactams, such as N-vinylpyrrolidone (NVP) and 1-vinylazonan-2-one; and acrylamides, such as methacrylamide and N,N-dimethylacrylamide (DMA).

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

Hydrophobic cross linkers would include methacrylates such as ethylene glycol dimethacrylate (EGDMA) and allyl methacrylate (AMA). In contrast to traditional silicon hydrogel monomer mixtures, the monomer mixtures containing the quaternized silicon monomer of the invention herein are relatively water soluble. This feature provides advantages over traditional silicon hydrogel monomer mixtures in that there is less risk of incompatibility phase separation resulting in hazy lenses and the polymerized materials are extractable with water. However, when desired traditional organic extraction methods may also be used. In addition, the extracted lenses demonstrate a good combination of oxygen permeability (Dk) and low modulus, properties known to be important to obtaining desirable contact lenses. Moreover, lenses prepared with the quaternized silicon monomers of the invention herein are wettable even without surface treatment, provide dry mold release, do not require solvents in the monomer mix (although solvents such as glycerol may be used), the extracted polymerized material is not cytotoxic and the surface is lubricious to the touch. In cases where the polymerized monomer mix containing the quaternized silicon monomers of the invention herein do not demonstrate a desirable tear strength, toughening agents such as TBE (4-t-butyl-2-hydroxycyclohexyl methacrylate) may be added to the monomer mix. Other strengthening agents are well known to those of ordinary skill in the art and may also be used when needed.

Although an advantage of the cationic silicon-containing monomers disclosed herein is that they are relatively water soluble and also soluble in their comonomers, an organic diluent may be included in the initial monomeric mixture. As used herein, the term "organic diluent" encompasses organic compounds which minimize incompatibility of the components in the initial monomeric mixture and are substantially nonreactive with the components in the initial mixture. Additionally, the organic diluent serves to minimize phase separation of polymerized products produced by polymerization of the monomeric mixture. Also, the organic diluent will generally be relatively non-inflammable.

Contemplated organic diluents include tert-butanol (TBA); diols, such as ethylene glycol and polyols, such as glycerol. Preferably, the organic diluent is sufficiently soluble in the extraction solvent to facilitate its removal from a cured article during the extraction step. Other suitable organic diluents would be apparent to a person of ordinary skill in the art.

The organic diluent is included in an amount effective to provide the desired effect. Generally, the diluent is included at 5 to 60% by weight of the monomeric mixture, with 10 to 50% by weight being especially preferred.

According to the present process, the monomeric mixture, comprising at least one hydrophilic monomer, at least one cationic silicon-containing monomer and optionally the organic diluent, is shaped and cured by conventional methods such as static casting or spincasting.

Lens formation can be by free radical polymerization such as azobisisobutyronitrile (AIBN) and peroxide catalysts using initiators and under conditions such as those set forth in U.S. Pat. No. 3,808,179, incorporated herein by reference. Photo initiation of polymerization of the monomer mixture as is well known in the art may also be used in the process of forming an article as disclosed herein. Colorants and the like may be added prior to monomer polymerization.

Subsequently, a sufficient amount of unreacted monomer and, when present, organic diluent is removed from the cured article to improve the biocompatibility of the article. Release of non-polymerized monomers into the eye upon installation of a lens can cause irritation and other problems. Unlike other monomer mixtures that must be extracted with flammable solvents such as isopropyl alcohol, because of the properties of the novel quaternized siloxane monomers disclosed herein, non-flammable solvents including water may be used for the extraction process.

Once the biomaterials formed from the polymerized monomer mix containing the cationic silicon containing monomers disclosed herein are formed they are then extracted to prepare them for packaging and eventual use. Extraction is accomplished by exposing the polymerized materials to various solvents such as water, tert-butanol, etc. for varying periods of time. For example, one extraction process is to immerse the polymerized materials in water for about three minutes, remove the water and then immerse the polymerized materials in another aliquot of water for about three minutes, remove that aliquot of water and then autoclave the polymerized material in water or buffer solution.

Following extraction of unreacted monomers and any organic diluent, the shaped article, for example an RGP lens, is optionally machined by various processes known in the art. The machining step includes lathe cutting a lens surface, lathe cutting a lens edge, buffing a lens edge or polishing a lens edge or surface. The present process is particularly advantageous for processes wherein a lens surface is lathe cut, since machining of a lens surface is especially difficult when the surface is tacky or rubbery.

Generally, such machining processes are performed before the article is released from a mold part. After the machining operation, the lens can be released from the mold part and hydrated. Alternately, the article can be machined after removal from the mold part and then hydrated.

EXAMPLES

All solvents and reagents were obtained from Sigma-Aldrich, Milwaukee, Wis., and used as received with the exception of aminopropyl terminated poly(dimethylsiloxane), 900-1000 and 3000 g/mol, obtained from Gelest, Inc., Morrisville, Pa., and methacryloxypropyltris(trimethylsiloxy)silane, obtained from Silar Laboratories, Scotia, N.Y., which were both used without further purification. The monomers 2-hydroxyethyl methacrylate and 1-vinyl-2-pyrrolidone were purified using standard techniques.

Analytical Measurements

NMR: $^1$H-Nuclear Magnetic Resonance (NMR) characterization was carried out using a 400 MHz Varian spectrometer using standard techniques in the art. Samples were dissolved in chloroform-d (99.8 atom % D), unless otherwise noted. Chemical shifts were determined by assigning the residual chloroform peak at 7.25 ppm. Peak areas and proton ratios were determined by integration of baseline separated peaks. Splitting patterns (s=singlet, d=doublet, t=triplet, q=quartet, m=multiplet, br=broad) and coupling constants (J/Hz) are reported when present and clearly distinguishable.

SEC: Size Exclusion Chromatography (SEC) analyses were carried out by injection of 100 µL of sample dissolved in tetrahydrofuran (THF) (5-20 mg/mL) onto a Polymer Labs PL Gel Mixed Bed E (×2) column at 35° C. using a Waters 515 HPLC pump and HPLC grade THF mobile phase flow rate of 1.0 mL/min, and detected by a Waters 410 Differential Refractometer at 35° C. Values of $M_n$, $M_w$, and polydispersity (PD) were determined by comparison to Polymer Lab Polystyrene narrow standards.

ESI-TOF MS: The electrospray (ESI) time of flight (TOF) MS analysis was performed on an Applied Biosystems Mariner instrument. The instrument operated in positive ion mode. The instrument was mass calibrated with a standard solution containing lysine, angiotensinogen, bradykinin (fragment 1-5) and des-Pro bradykinin. This mixture provides a seven-point calibration from 147 to 921 m/z. The applied voltage parameters were optimized from signal obtained from the same standard solution.

Stock solutions of the polymer samples were prepared as 1 mg/mL in tetrahydrofuran (THF). From these stock solutions, samples were prepared for ESI-TOF MS analysis as 30 µM solutions in isopropanol (IPA) with the addition of 2% by volume saturated NaCl in IPA. Samples were directly infused into the ESI-TOF MS instrument at a rate of 35 µL/min.

Mechanical properties and Oxygen Permeability: Modulus and elongation tests were conducted according to ASTM D-1708a, employing an Instron (Model 4502) instrument where the hydrogel film sample is immersed in borate buffered saline; an appropriate size of the film sample is gauge length 22 mm and width 4.75 mm, where the sample further has ends forming a dog bone shape to accommodate gripping of the sample with clamps of the Instron instrument, and a thickness of 200+50 microns.

Oxygen permeability (also referred to as Dk) was determined by the following procedure. Other methods and/or instruments may be used as long as the oxygen permeability values obtained therefrom are equivalent to the described method. The oxygen permeability of silicone hydrogels is measured by the polarographic method (ANSI Z80.20-1998) using an O2 Permeometer Model 201T instrument (Createch, Albany, Calif. USA) having a probe containing a central, circular gold cathode at its end and a silver anode insulated from the cathode. Measurements are taken only on pre-inspected pinhole-free, flat silicone hydrogel film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath containing circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For silicone hydrogel films, it is frequently useful to employ a Teflon polymer membrane, e.g., having a circular disk shape, between the probe cathode and the film sample. In such cases, the Teflon membrane is first placed on the pre-moistened cathode, and then the film sample is placed on the Teflon membrane, ensuring no air bubbles or excess PBS exists beneath the Teflon membrane or film sample. Once measurements are collected, only data with correlation coefficient value (R2) of 0.97 or higher should be entered into the calculation of Dk value. At least two Dk measurements per thickness, and meeting R2 value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PHB and allowed to equilibrate for at least 12 hours. The instruments are regularly cleaned and regularly calibrated using RGP standards. Upper and lower limits are established by calculating a +/−8.8% of the Repository values established by William J. Benjamin, et al., The Oxygen Permeability of Reference Materials, Optom Vis Sci 7 (12s): 95 (1997), the disclosure of which is incorporated herein in its entirety:

| Material Name | Repository Values | Lower Limit | Upper Limit |
|---|---|---|---|
| Fluoroperm 30 | 26.2 | 24 | 29 |
| Menicon EX | 62.4 | 56 | 66 |
| Quantum II | 92.9 | 85 | 101 |

Abbreviations
 NVP 1-Vinyl-2-pyrrolidone
 TRIS Methacryloxypropyltris(trimethylsiloxy)silane
 HEMA 2-Hydroxyethyl methacrylate
 v-64 2,2'-Azobis(2-methylpropionitrile)
 PG 1,3-Propanediol
 EGDMA Ethylene glycol dimethacrylate
 SA 2-[3-(2H-Benzotriazol-2-yl)-4-hydroxyphenyl]ethyl methacrylate
 IMVT 1,4-bis[4-(2-methacryloxyethyl)phenylamino]anthraquinone Unless otherwise specifically stated or made clear by its usage, all numbers used in the examples should be considered to be modified by the term "about" and to be weight percent.

Example 1

Synthesis of 3-(chloroacetylamido)propyl Terminated poly(dimethylsiloxane)

To a vigorously stirred biphasic mixture of a solution of 3-aminopropyl terminated poly(dimethylsiloxane) (97.7 g, 3000 g/mol) obtained from Gelest, Inc., Morrisville, Pa. in dichloromethane (350 mL) and NaOH$_{(aq)}$ (0.75 M, 150 mL) at 0° C. was added a solution of chloroacetyl chloride (8 mL, 0.1 mol) in dichloromethane (50 mL) dropwise. Following an additional 1 hour at ambient temperature, the organic layer was separated and stirred 5 hours over silica gel (25 g) and Na$_2$SO$_4$ (25 g) and filtered. Solvents were removed at reduced pressure to afford the product as a colorless liquid (85 g, 83%): $^1$H NMR (CDCl$_3$, 400 MHz) δ 6.64 (br, 2H), 4.05 (s, 4H), 3.29 (q, J=7 Hz, 4H), 1.60-1.52 (m, 4H), 0.56-0.52 (m, 4H), 0.06 (s, approximately 264H); GPC: M$_w$ 3075 g/mol, PD 1.80. The mass spectrum of this sample indicated a mass distribution of singly charged oligomers having a repeat unit mass of 74 Da. This corresponds to the targeted dimethyl siloxane (C2H6SiO) repeat unit chemistry. The targeted end group nominal mass for this sample is 326 Da (C$_{12}$H$_{24}$N$_2$O$_2$SiCl$_2$) and the required sodium charge agent has a mass of 23 Da (Na). The mass peaks in the distribution for this sample correspond to a nominal mass sequence of (74×n+326+23) where n is the number of repeat units. There is a good match between the experimental and theoretical isotopic distribution patterns for the oligomers evaluated.

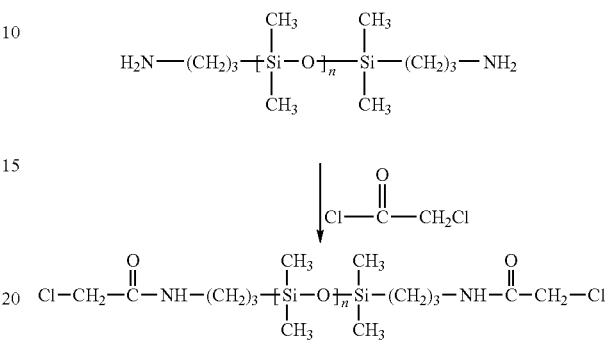

Example 2

Synthesis of 3-(bromoacetylamido)propyl Terminated poly(dimethylsiloxane)

Aminopropyl terminated poly(dimethylsiloxane) (50.2 g, 3000 g/mol) was reacted with bromoacetyl chloride in substantially the same manner as described in the example 1 to afford the product as a viscous, colorless oil (40 g, 74%): $^1$H NMR (CDCl$_3$, 400 MHz) δ 6.55 (br, 2H), 3.89 (s, 4H), 3.27 (q, J=7 Hz, 4H), 1.60-1.52 (m, 4H), 0.54 (t, J=7 Hz, 4H), 0.06 (s, approximately 348H). GPC: M$_w$ 5762 g/mol, PD 1.77. The mass spectrum of this sample indicated a mass distribution of singly charged oligomers having a repeat unit mass of 74 Da. This corresponds to the targeted dimethyl siloxane (C2H6SiO) repeat unit chemistry. The targeted end group nominal mass for this sample is 414 Da (C$_{12}$H$_{24}$N$_2$O$_2$SiBr$_2$) and the required sodium charge agent has a mass of 23 Da (Na). The mass peaks in the distribution for this sample correspond to a nominal mass sequence of (74×n+414+23) where n is the number of repeat units. There is a good match between the experimental and theoretical isotopic distribution patterns for the oligomers evaluated.

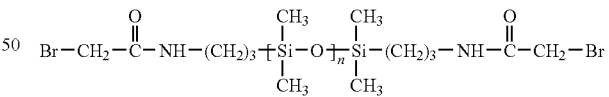

Example 3

Synthesis of Cationic Methacrylate Chloride Terminated poly(dimethylsiloxane)

To a solution of 3-(chloroacetylamido)propyl end-capped poly(dimethylsiloxane) (19.96 g) from example 1 in ethyl acetate (25 mL) was added 2-(dimethylamino)ethyl methacrylate (3.40 mL, 20.1 mmol) and the mixture was heated 39 hours at 60° C. under a nitrogen atmosphere in the dark. The resulting solution was stripped of solvent and/or reagent at reduced pressure affording the product (23.1 g) containing a residual amount of 2-(dimethylamino)ethyl methacrylate (<10 w/w %) that is easily quantified by $^1$H NMR analysis: $^1$H NMR (CDCl$_3$, 400 MHz) δ 9.23 (br, 2H), 6.07 (s, 2H), 5.60 (s, 2H), 4.71 (s, 4H), 4.65-4.63 (m, 4H), 4.18 (br, 4H) 3.47 (s, 12 H), 3.19-3.13 (m, 4H), 1.88 (s, 6H), 1.53-1.49 (m, 4H), 0.51-0.47 (m, 4H), 0.01 (s, approximately 327H). The mass spectrum of this sample indicated a mass distribution of doubly charged oligomers having a repeat unit mass of 37 Da. When deconvoluted this corresponds to a repeat unit mass of 74 Da (37 Da×2). This corresponds to the targeted dimethyl siloxane (C$_2$H$_6$SiO) repeat unit chemistry. The targeted end group nominal mass for this sample is 570 Da (C$_{28}$H$_{54}$N$_4$O$_6$Si). The end group chemistry contains two quaternary nitrogen atoms and thus no additional charge agent is required. The two quaternary nitrogen (N$^+$) atoms also explain the presence of the doubly charged mass peaks. The mass peaks in the distribution for this sample correspond to a nominal mass sequence of ((74/2)×n+570) where n is the number of repeat units. There is a good match between the experimental and theoretical isotopic distribution patterns for the oligomers evaluated.

(dimethylamino)propyl]methacrylamide (4.90 mL, 27.0 mmol) in substantially the same fashion as described in example 3 to afford cationic methacrylamide chloride terminated poly(dimethylsiloxane) (41.5 g) with a residual amount of N-[3-(dimethylamino)propyl]methacrylamide (<10 w/w %) that is easily quantified by $^1$H NMR analysis: $^1$H NMR (CDCl$_3$, 400 MHz) δ 9.19 (br, 2H), 7.68 (br, 2H), 5.87 (s, 2H), 5.33 (br, 2 h), 4.45 (s, 4 H), 3.72-3.69 (m, 4H), 3.44-3.40 (m, 4H), 3.33 (s, 12H), 3.21-3.16 (m, 4H), 2.21-2.17 (m, 4H), 1.95 (s, 6H), 1.55-1.51 (m, 4H), 0.54-0.49 (m, 4H), 0.04 (s, approximately 312H). The mass spectrum of this sample indicated a mass distribution of doubly charged oligomers having a repeat unit mass of 37 Da. When deconvoluted this corresponds to a repeat unit mass of 74 Da (37 Da×2). This corresponds to the targeted dimethyl siloxane (C$_2$H$_6$SiO) repeat unit chemistry. The targeted end group nominal mass for this sample is 596 Da (C$_{30}$H$_{60}$N$_6$O$_4$Si). The end group

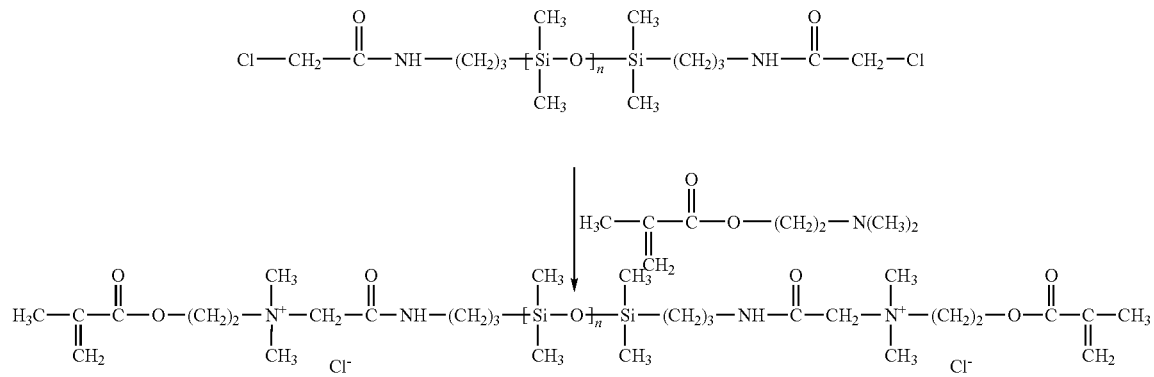

Example 4

Synthesis of Cationic Methacrylamide Chloride Terminated poly(dimethylsiloxane)

3-(Chloroacetylamido)propyl end-capped poly(dimethylsiloxane) from example 1 (36.9 g) was reacted with N-[3- chemistry contains two quaternary nitrogen atoms and thus no additional charge agent is required. The two quaternary nitrogen (N$^+$) atoms also explain the presence of the doubly charged mass peaks. The mass peaks in the distribution for this sample correspond to a nominal mass sequence of ((74/2)×n+596) where n is the number of repeat units. There is a good match between the experimental and theoretical isotopic distribution patterns for the oligomers evaluated.

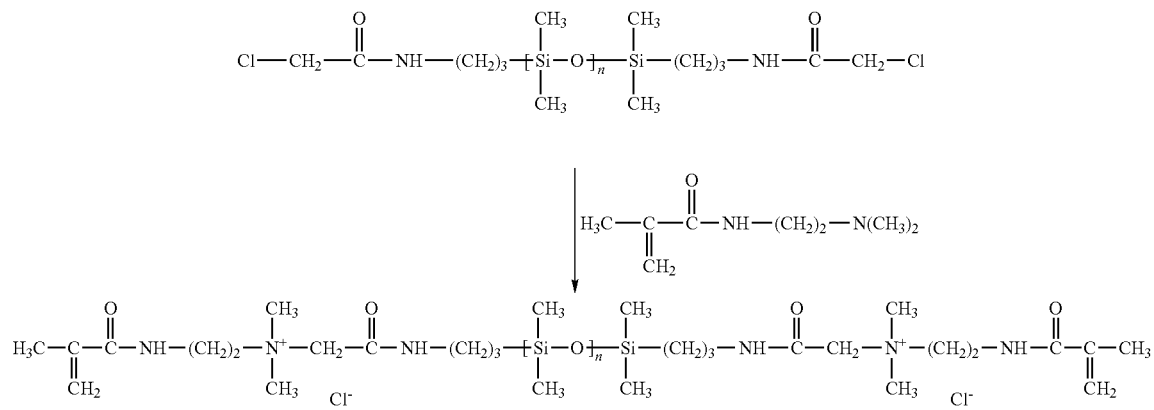

Example 5

Synthesis of Cationic Methacrylate Bromide Terminated poly(dimethylsiloxane)

3-(bromoacetylamido)propyl terminated poly(dimethylsiloxane) from example 2 (15.0 g) was reacted in substantially the same manner as described in example 3 above to afford

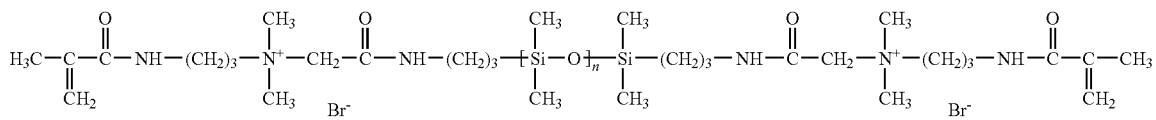

cationic methacrylate bromide terminated poly(dimethylsiloxane) (17.8 g) as a highly viscous liquid: $^1$H NMR (CDCl$_3$, 400 MHz) δ 8.79 (br, 2H), 6.12 (s, 2H), 5.65 (s, 2H), 4.76 (s, 4H), 4.66 (br, 4H), 4.20 (br, 4H), 3.49 (s, 12H), 3.21 (t, J=7 Hz, 4H), 1.93 (s, 6H), 1.59-1.51 (m, 4H), 0.55-0.51 (m, 4H), 0.04 (s, approximately 400H). The mass spectrum of this sample indicated a mass distribution of doubly charged oligomers having a repeat unit mass of 37 Da. When deconvoluted this corresponds to a repeat unit mass of 74 Da (37 Da×2). This corresponds to the targeted dimethyl siloxane (C$_2$H$_6$SiO) repeat unit chemistry. The targeted end group nominal mass for this sample is 570 Da (C$_{28}$H$_{54}$N$_4$O$_6$Si). The end group chemistry contains two quaternary nitrogen atoms and thus no additional charge agent is required. The two quaternary nitrogen (N$^+$) atoms also explain the presence of the doubly charged mass peaks. The mass peaks in the distribution for this sample correspond to a nominal mass sequence of ((74/2)×n+570) where n is the number of repeat units. There is a good match between the experimental and theoretical isotopic distribution patterns for the oligomers evaluated.

Example 6

Synthesis of Cationic Methacrylamide Bromide Terminated poly(dimethylsiloxane)

3-(bromoacetylamido)propyl terminated poly(dimethylsiloxane) from example 2 (15.0 g) was reacted in substantially the same manner as described in example 3 above to afford cationic methacrylamide bromide terminated poly(dimethylsiloxane) as a highly viscous liquid (16.7 g): $^1$H NMR (CDCl$_3$, 400 MHz) δ 8.76 (br, 2H), 7.44 (br, 2H), 5.87 (s, 2H), 5.33 (s, 2H), 4.47 (s, 4H), 3.77-3.73 (m, 4H), 3.43-3.40 (s, 4H), 3.35 (s, 12H), 3.22-3.17 (m, 4H), 3.24-3.00 (m, 4H), 1.96 (s, 6H), 1.58-1.50 (m, 4H), 0.54-0.50 (m, 4H), 0.04 (s, approximately 387H). The mass spectrum of this sample indicated a mass distribution of doubly charged oligomers having a repeat unit mass of 37 Da. When deconvoluted this corresponds to a repeat unit mass of 74 Da (37 Da×2). This corresponds to the targeted dimethyl siloxane (C$_2$H$_6$SiO) repeat unit chemistry. The targeted end group nominal mass for this sample is 596 Da (C$_{30}$H$_{60}$N$_6$O$_4$Si). The end group chemistry contains two quaternary nitrogen atoms and thus no additional charge agent is required. The two quaternary nitrogen (N$^+$) atoms also explain the presence of the doubly charged mass peaks. The mass peaks in the distribution for this sample correspond to a nominal mass sequence of ((74/2)×n+596) where n is the number of repeat units. There is a good match between the experimental and theoretical isotopic distribution patterns for the oligomers evaluated.

Example 7

Synthesis of Cationic Methacrylate Chloride Terminated poly(dimethylsiloxane)

3-Aminopropyl terminated poly(dimethylsiloxane) (g, 900-1000 g/mol) was reacted in two steps in substantially the same manner as described in examples 1 and 3 to afford cationic methacrylate chloride terminated poly(dimethylsiloxane) as a highly viscous fluid: $^1$H NMR (CDCl$_3$, 400 MHz) δ 9.26 (br, 2H), 6.12 (s, 2H), 5.67 (s, 2H), 4.75 (s, 4H), 4.66 (br, 4H), 4.14 (br, 4H), 3.47 (s, 12 H), 3.22 (br, 4H), 2.06 (br, 4H), 1.93 (s, 6H), 1.59-1.52 (m, 4H), 0.56-0.52 (m, 4H), 0.05 (s, approximately 192H).

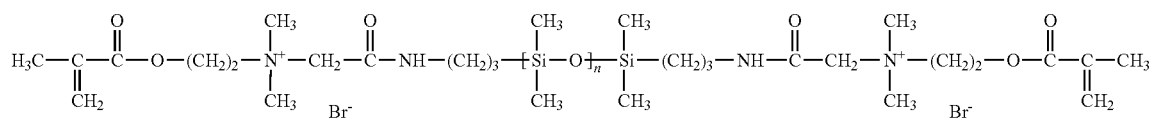

Examples 8-12

Polymerization, Processing and Properties of Films Containing Cationic Siloxanyl Prepolymers Liquid monomer solutions containing cationic end-capped poly(dimethylsiloxane) prepolymers from examples 3-7 above, along with other additives common to ophthalmic materials (diluent, initiator, etc.) were clamped between silanized glass plates at various thicknesses and polymerized using thermal decomposition of the free-radical generating additive by heating 2 h at 100° C. under a nitrogen atmosphere. Each of the formulations listed in table 1 afforded a transparent, tack-free, insoluble film.

TABLE 1

Formulations containing cationic end-capped poly(dimethylsiloxane)

| Example | Ex. 3 | Ex. 4 | Ex. 5 | Ex. 6 | Ex. 7 | NVP | HEMA | TRIS | PG | EGDMA | v-64 |
|---|---|---|---|---|---|---|---|---|---|---|---|
| 8 | 19.2 | | | | | 34.4 | | 48.9 | | | 0.5 |
| 9 | 14.2 | | | | | 37.8 | 18.9 | 23.6 | 5.0 | | 0.5 |
| 10 | | 14.2 | | | | 37.9 | 19.0 | 23.7 | 4.7 | | 0.5 |
| 11 | | | 17.3 | | | 39.4 | 16.8 | 27.9 | 3.6 | 0.2 | 0.5 |
| 12 | | | | 25.8 | | 24.3 | 24.9 | 24.2 | | 0.2 | 0.5 |
| 13 | 7.0 | | | | 7.0 | 36.9 | 19.4 | 23.1 | 4.9 | | 0.5 |

Films were removed from glass plates and hydrated/extracted in deionized H$_2$O for a minimum of 4 hours, transferred to fresh deionized H2O and autoclaved 30 min at 121° C. The cooled films were then analyzed for selected properties of interest in ophthalmic materials as described in table 2. Mechanical tests were conducted in borate buffered saline according to ASTM D-1708a, discussed above. The oxygen permeabilities, reported in Dk (or barrer) units, were measured in phosphate buffered saline at 35° C., using acceptable films with three different thicknesses, as discussed above.

TABLE 2

Properties of processed films containing cationic end-capped poly(dimethylsiloxane)

| Example | Water content (w/w %) | Dk (barrers) | Modulus (g/mm$^2$)* | Tear (g/mm)* |
|---|---|---|---|---|
| 8 | 36.5 | 117 | 210(21) | 16(2) |
| 9 | 52.1 | 60 | 75(3) | 7.0(5) |
| 10 | 51.4 | 62 | 101(14) | 5(1) |
| 11 | 41.5 | 74 | 123(13) | 9(1) |
| 12 | 31.9 | 89 | 180(12) | 8.0(4) |
| 13 | 49.4 | 53 | 111(4) | 4.0(3) |

*number in parentheses indicates standard deviation of final digit(s)

Example 14

Polymerization and Processing of Ophthalmic Lenses Containing Cationic End-Capped poly(dimethylsiloxane)

40 μL aliquots of a soluble, liquid monomer mix containing 13.9 parts by weight of the product from example 3, 23.3 parts TRIS, 41.8 parts NVP, 13.9 parts HEMA, 5 parts PG, 0.5 parts v-64, 1.5 parts SA, and 60 ppm IMVT were sealed between poly(propylene) anterior and posterior contact lens moulds under an inert nitrogen atmosphere, transferred to an oven and heated under an inert nitrogen atmosphere 2 h at 100° C. The cooled mold pairs were separated and the dry lens released from the mold, hydrated/extracted twice in deionized H2O for a minimum of 3 min, transferred to and sealed in an autoclave vial containing a buffered saline solution and autoclaved 30 min at 121° C. affording optically transparent, blue-tinted ophthalmic lenses with a refractive index of 1.4055+/−0.0005.

Example 15

Preparation of RD-1778

Overview

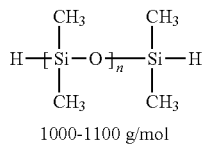

1000-1100 g/mol

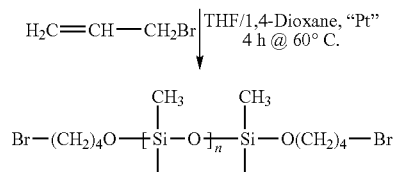

Column purification (silica gel, pentane)

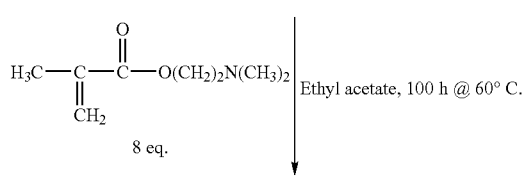

8 eq.

-continued

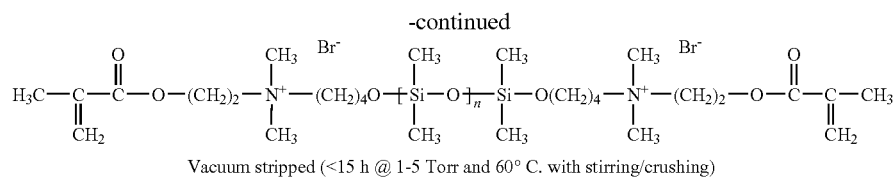

Vacuum stripped (<15 h @ 1-5 Torr and 60° C. with stirring/crushing)

Materials

The reagents allyl bromide, 2-(dimethylamino)ethyl methacrylate (98%; IMPORTANT: Stabilized by 2000 ppm MEHQ), 10% platinum-1,3-divinyl-1,1,3,3-tetramethyldisiloxane complex in xylenes, chloroform-d (99.8 atom % D), n-pentane (HPLC grade), anhydrous ethyl acetate (99.8%), anhydrous tetrahydrofuran, anhydrous 1,4-dioxane, silica gel 60 (70-230 mesh ASTM) were purchased from Sigma-Aldrich, Milwaukee, Wis., and used without further purification. The reagent hydride terminated poly(dimethylsiloxane) (average molecular weight 1000-1100 g/mol) was purchased from Gelest, Inc., Morrisville, Pa.

Analytical Methods

NMR: $^1$H-NMR characterization was carried out using a 400 MHz Varian spectrometer using standard techniques in the art. Samples were dissolved in chloroform-d (99.8 atom % D), unless otherwise noted. Chemical shifts were determined by assigning the residual chloroform peak at 7.25 ppm. Peak areas and proton ratios were determined by integration of baseline separated peaks. Splitting patterns (s=singlet, d=doublet, t=triplet, q=quartet, m=multiplet, br=broad) and coupling constants (J/Hz) are reported when present and clearly distinguishable.

SEC: Size Exclusion Chromatography (SEC) analyses were carried out by injection of 100 μL of sample dissolved in tetrahydrofuran (THF) (5-20 mg/mL) onto a Polymer Labs PL Gel Mixed Bed E (×2) column at 35° C. using a Waters 515 HPLC pump and HPLC grade THF mobile phase flow rate of 1.0 mL/min, and detected by a Waters 410 Differential Refractometer at 35° C. Values of $M_n$, $M_w$, and polydispersity (PD) were determined by comparison to Polymer Lab Polystyrene narrow standards.

Preparation

Step 1: Hydrosilation. To a solution of hydride terminated poly(dimethylsiloxane) (99.3 g, 1000-1100 $M_n$) and allyl bromide (25 mL, 287 mmol, 3.0 eq.) in tetrahydrofuran/1,4-dioxane (2:1 v/v, 570 mL) in a round bottomed flask equipped with stirring apparatus, water condenser, and nitrogen purge was added 10% platinum-1,3-divinyl-1,1,3,3-tetramethyldisiloxane complex in xylenes (0.7 mL) and the solution was heated 4 h at 60° C. The cooled solution was concentrated under reduced pressure, redissolved in pentane (250 mL), passed through a chromatography column packed with silica gel (200 g) details in materials section and pentane, and flushed with an additional 300 mL pentane. The colorless solution was concentrated under reduced pressure (approximately 25 Torr), then stripped under high vacuum (approximately 1 Torr) to constant weight to afford 112.12 g (90.1% yield) clear liquid product (1316 g/mol).

Step 2: Quaternization. The colorless liquid product from step 1 (112.12 g) was then dissolved in ethyl acetate (150 mL, 1.3 mL/g) and treated with 2-(dimethylamino)ethyl methacrylate (116 mL, 680 mmol, approximately 8 eq.) in a round bottomed flask equipped with magnetic stir bar, and sealed with a nitrogen purge for a half hour. The reaction remained under positive nitrogen pressure upon removal of the nitrogen purge such that the vessel withstands the slight headspace pressure during subsequent heating. The reaction was then heated 100 h at 60° C. and in the dark. (NOTE: Due to the presence of polymerizable moiety, the reaction must be carefully monitored and controlled to avoid gelation, e.g. using a jacketed round bottom, oil bath, etc.). The cooled solution was then concentrated under reduced pressure (approximately 25 Torr and 40° C.). The resulting product mixture, ranging from viscous liquid to partial solid and clear to amber in color, was stripped at high vacuum (<1 Torr) and 60° C. to remove residual ethyl acetate and N,N-dimethylamino(ethyl methacrylate). The hot liquid will begin to solify into an amorphous solid during the stripping, requiring frequent stirring/scraping/crushing of the product mixture, especially toward the end of stripping. The stripping is complete when the product is solidified throughout by visual appearance and no more residual monomer is being collected. The resulting waxy solid product, ranging from colorless to light amber in color is then stored in amber vials at low temperature.

Analytical $^1$H NMR: (CDCl$_3$, 400 MHz) δ 6.19 (s, 0.01H), 5.66 (s, 0.01), 4.64 (br, 0.02H), 1.76 (br, 0.02H), 3.70-3.64 (m, 0.04H), 3.50 (0.06H), 1.94-1.83 (m, 0.05H), 1.63-1.55 (m, 0.02H), 0.05 (s, 0.78H). PDMS chain length (x), molecular weight, percent conversion, and residual monomer/solvent are estimated using integrations of the product peaks at δ 5.66 (vinyl H of product end-cap, V), 5.55 (vinyl H of residual N,N-Dimethylamino(ethyl methacrylate)), 1.59 (CH$_2$ of PDMS alkyl end-cap, A), and 0.05 ppm (—CH$_3$ of PDMS backbone, P), using the following calculations:

Chain length (n)=(P×2)/(A×3)

Molecular weight (g/mol)=n×74+558

Conversion (%)=[(V×2)/(A)]×100

Mole fraction residual DMAEMA (d)=(D)/[(V/2)+(D)]

Residual DMAEMA (w/w %)=[(d×157)/([d×157]+[(1−d)×MW])]×100

ESI-TOF. The mass spectrum of this sample indicated a mass distribution of doubly charged oligomers having a repeat unit mass of 37 Da. When deconvoluted this corresponds to a repeat unit mass of 74 Da (37 Da×2). This corresponds to the targeted dimethyl siloxane (C$_2$H$_6$SiO) repeat unit chemistry. The end group chemistry contains two quaternary nitrogen atoms and thus no additional charge agent is required. The two quaternary nitrogen (N$^+$) atoms also explain the presence of the doubly charged mass peaks.

Example 16

Preparation of RD-1799

Overview

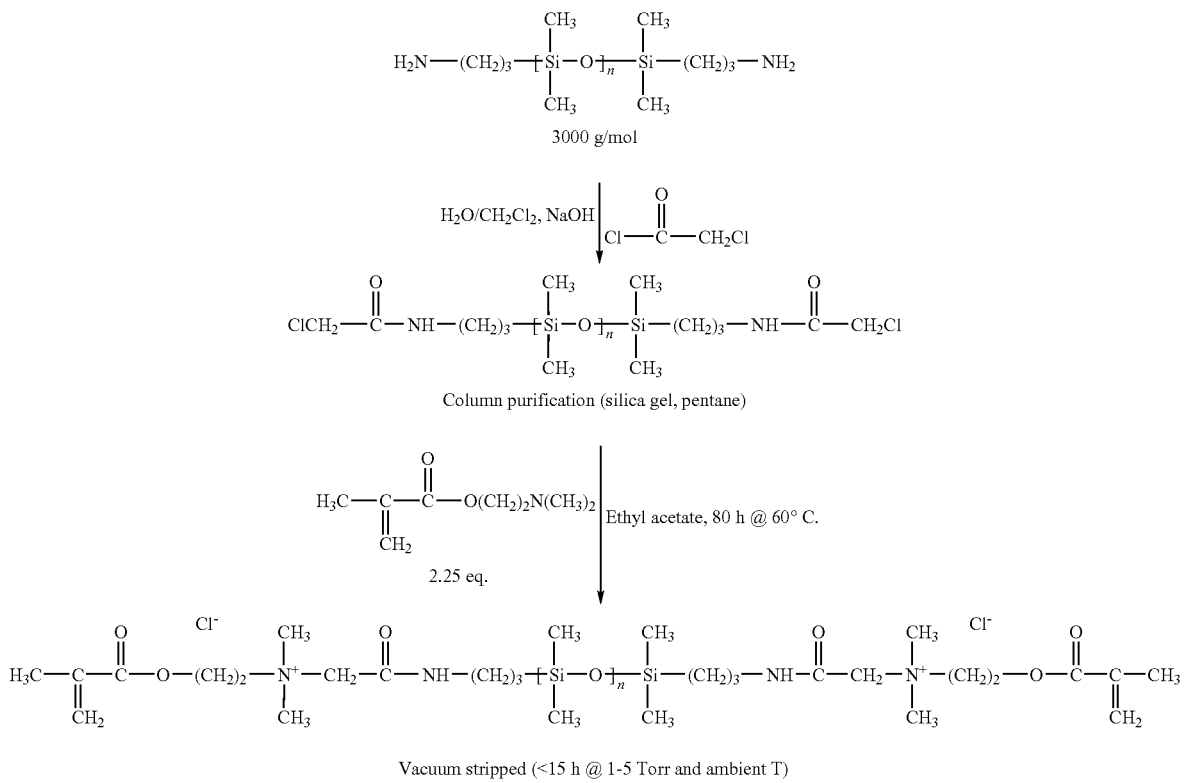

Materials

The reagents chloroacetyl chloride (98%), 2-(dimethylamino)ethyl methacrylate (98%; IMPORTANT: Stabilized by 2000 ppm MEHQ), chloroform-d (99.8 atom % D), n-pentane (HPLC grade), anhydrous ethyl acetate (99.8%), sodium hydroxide, silica gel 60 (70-230 mesh ASTM) were purchased from Sigma-Aldrich, Milwaukee, Wis., and used without further purification. The reagent aminopropyl terminated poly(dimethylsiloxane) (average molecular weight 2500 g/mol) was purchased from Gelest, Inc., Morrisville, Pa.

Analytical Methods

ESI-TOF MS: The electrospray (ESI) time of flight (TOF) MS analysis was performed on an Applied Biosystems Mariner instrument. The instrument operated in positive ion mode. The instrument was mass calibrated with a standard solution containing lysine, angiotensinogen, bradykinin (fragment 1-5) and des-Pro bradykinin. This mixture provides a seven-point calibration from 147 to 921 m/z. The applied voltage parameters were optimized from signal obtained from the same standard solution. For exact mass measurements poly (ethylene glycol) (PEG), having a nominal M, value of 400 Da, was added to the sample of interest and used as an internal mass standard. Two PEG oligomers that bracketed the sample mass of interest were used to calibrate the mass scale. Samples were prepared as 30 µM solutions in isopropanol (IPA) with the addition of 2% by volume saturated NaCl in IPA. Samples were directly infused into the ESI-TOF MS instrument at a rate of 35 µL/min. A sufficient resolving power (6000 RP m/$\Delta$m FWHM) was achieved in the analysis to obtain the monoistopic mass for each sample. In each analysis the experimental monoisotopic mass was compared to the theoretical monoisotopic mass as determined from the respective elemental compositions. In each analysis the monoisotopic mass comparison was less than 10 ppm error. It should be noted that uncharged samples have a sodium (Na) atom included in their elemental composition. This Na atom occurs as a necessary charge agent added in the sample preparation procedure. Some samples do not require an added charge agent since they contain a charge from the quaternary nitrogen inherent to their respective structure.

NMR: $^1$H-NMR characterization was carried out using a 400 MHz Varian spectrometer using standard techniques in the art. Samples were dissolved in chloroform-d (99.8 atom % D), unless otherwise noted. Chemical shifts were determined by assigning the residual chloroform peak at 7.25 ppm. Peak areas and proton ratios were determined by integration of baseline separated peaks. Splitting patterns (s=singlet, d=doublet, t=triplet, q=quartet, m=multiplet, br=broad) and coupling constants (J/Hz) are reported when present and clearly distinguishable.

SEC: Size Exclusion Chromatography (SEC) analyses were carried out by injection of 100 µL of sample dissolved in tetrahydrofuran (THF) (5-20 mg/mL) onto a Polymer Labs PL Gel Mixed Bed E (×2) column at 35° C. using a Waters 515 HPLC pump and HPLC grade THF mobile phase flow rate of 1.0 mL/min, and detected by a Waters 410 Differential Refractometer at 35° C. Values of $M_n$, $M_w$, and polydispersity (PD) were determined by comparison to Polymer Lab Polystyrene narrow standards.

Preparation

Step 1: Amidation. To a vigorously stirred biphasic mixture of 3-aminopropyl terminated poly(dimethylsiloxane) (97.7 g) in dichloromethane (122 mL) and NaOH$_{(aq)}$ (5.0 M, 62 mL) at 0° C. was added a solution of chloroacetyl chloride (9.31 mL, 0.117 mol) in dichloromethane (23 mL) dropwise over 30 min. Following an additional 1.5 h at 0° C., the organic layer was separated and dried over magnesium sulfate. The clear liquid was decanted and passed through a chromatography column packed with silica gel (150 g) and methylene chloride. An additional 200 mL of methylene chloride was passed through the column and solvents were removed at reduced pressure to afford the product as a viscous, colorless liquid (85 g, 83%).

$^1$H NMR: (CDCl$_3$, 400 MHz) δ 6.64 (br, 2H), 4.05 (s, 4H), 3.29 (q, J=7 Hz, 4 H), 1.60-1.52 (m, 4H), 0.56-0.52 (m, 4H), 0.06 (s, approximately 264H).

SEC: M$_w$ 3075 g/mol, PD 1.80.

ESI-TOF: The mass spectrum of this sample indicated a mass distribution of singly charged oligomers having a repeat unit mass of 74 Da. This corresponds to the targeted dimethyl siloxane (C2H6SiO) repeat unit chemistry. The targeted end group nominal mass for this sample is 326 Da (Cl$_2$H$_{24}$N$_2$O$_2$SiCl$_2$) and the required sodium charge agent has a mass of 23 Da (Na). The mass peaks in the distribution for this sample correspond to a nominal mass sequence of (74×n+326+23) where n is the number of repeat units. There is a good match between the experimental and theoretical isotopic distribution patterns for the oligomers evaluated.

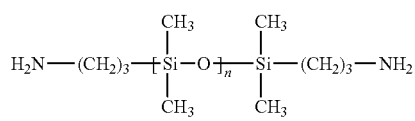

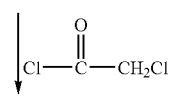

-continued

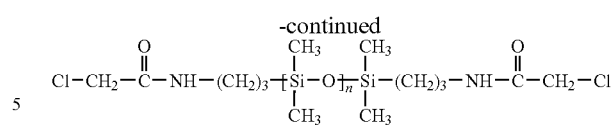

Step 2: Quaternization. A solution of 3-(chloroacetylamido)propyl end-capped poly(dimethylsiloxane) (19.96 g, 3200 g/mol) from step 1, ethyl acetate (19 mL), and para-methoxyphenol (20 mg, 1000 ppm) in a round-bottomed flask equipped with stir bar, was treated with 2.25 equivalents 2-(dimethylamino)ethyl methacrylate. To account for slight differences in molecular weight distributions, 2-(dimethylamino)ethyl methacrylate was added in small quantities, homogenized with stirring, then aliquots of reaction mixture were removed, diluted in chloroform-d and analyzed via $^1$H NMR integration of the multiplet peak at 0.56-0.52 ppm (4 protons per end-capped PDMS) versus the singlet peak at 5.55 ppm (1 proton per 2-(dimethylamino)ethyl methacrylate) to obtain accurate quantification of stoichiometry, then adjusted as needed with additional 2-(dimethylamino)ethyl methacrylate. The vessel was sealed and purged with nitrogen 30 min. The purge was removed and positive nitrogen pressure remained such that the vessel withstands the slight headspace pressure during subsequent heating. The reaction was then heated 80 h at 60° C. and in the dark. (NOTE: Due to the presence of polymerizable moiety, the reaction must be carefully monitored and controlled to avoid gelation, e.g. using a jacketed round bottom, oil bath, etc.). The cooled solution was then concentrated under reduced pressure (approximately 25 Torr and 40° C.), then stripped at high vacuum (<1 Torr) and ambient temperature to constant weight (4-15 h) affording the product as a highly viscous liquid ranging from colorless to yellow containing a residual amount of 2-(dimethylamino)ethyl methacrylate (<10 w/w %) that is then transferred into amber bottles and stored cold.

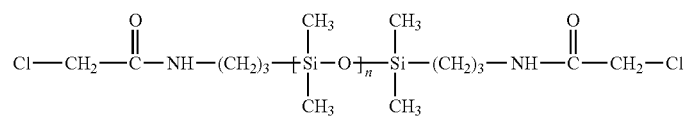

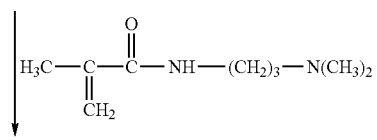

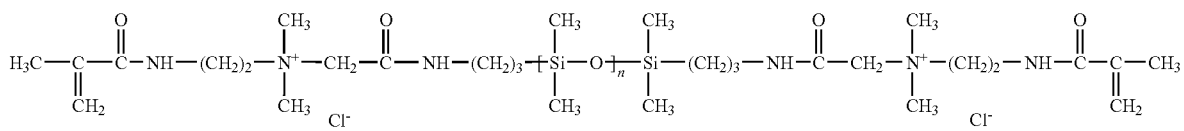

Analytical $^1$H NMR: (CDCl$_3$, 400 MHz) δ 9.23 (br, 2H), 6.07 (s, 2H), 5.60 (s, 2H), 4.71 (s, 4H), 4.65-4.63 (m, 4H), 4.18 (br, 4H) 3.47 (s, 12H), 3.19-3.13 (m, 4H), 1.88 (s, 6H), 1.53-1.49 (m, 4H), 0.51-0.47 (m, 4H), 0.01 (s, approximately 327H). PDMS chain length (x), molecular weight, percent conversion, and residual monomer/solvent are estimated using integrations of the product peaks at δ 5.60 (vinyl H of product end-cap, V), 5.55 (vinyl H of residual N,N-Dimethylamino (ethyl methacrylate)), 0.51-0.47 (CH$_2$ of PDMS alkyl end-cap, A), and 0.01 ppm (—CH$_3$ of PDMS backbone, P), using the following calculations:

Chain length (n)=(P×2)/(A×3)
Molecular weight (g/mol)=n×74+584
Conversion (%)=[(V×2)/(A)]×100
Mole fraction residual DMAEMA (d)=(D)/[(V/2)+(D)]
Residual DMAEMA (w/w %)=[(d×157)/([d×157]+[(1−d)×MW])]×100

ESI-TOF: The mass spectrum of this sample indicated a mass distribution of doubly charged oligomers having a repeat unit mass of 37 Da. When deconvoluted this corresponds to a repeat unit mass of 74 Da (37 Da×2). This corresponds to the targeted dimethyl siloxane (C$_2$H$_6$SiO) repeat unit chemistry. The targeted end group nominal mass for this sample is 570 Da (C$_{28}$H$_{54}$N$_4$O$_6$Si). The end group chemistry contains two quaternary nitrogen atoms and thus no additional charge agent is required. The two quaternary nitrogen (N$^+$) atoms also explain the presence of the doubly charged mass peaks. The mass peaks in the distribution for this sample correspond to a nominal mass sequence of ((74/2)×n+570) where n is the number of repeat units. There is a good match between the experimental and theoretical isotopic distribution patterns for the oligomers evaluated.

Example 17

Preparation of RD-1799-B and RD-1778-B

Overview

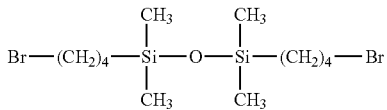

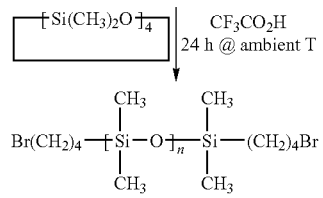

NaHCO$_3$ neutralization, filtered, stripped 2 h at 1-5 Torr and 80° C.

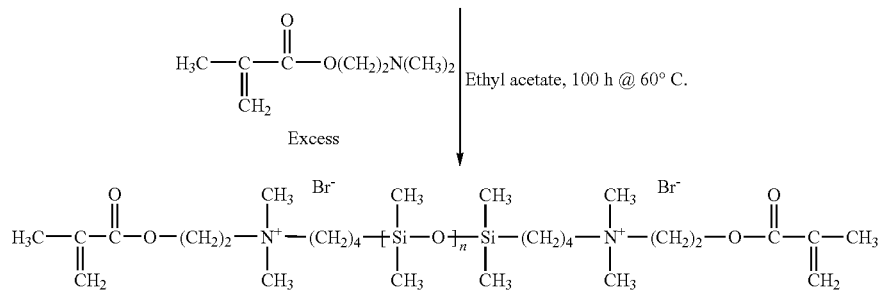

Vacuum stripped (<15 h @ 1-5 Torr and 60° C. with stirring/crushing)

Materials

The reagents 2-(dimethylamino)ethyl methacrylate (98%; IMPORTANT: Stabilized by 2000 ppm MEHQ), trifluoroacetic acid, chloroform-d (99.8 atom % D), n-pentane (HPLC grade), anhydrous ethyl acetate (99.8%), sodium hydroxide, silica gel 60 (70-230 mesh ASTM) were purchased from Sigma-Aldrich, Milwaukee, Wis., and used without further purification. The reagent Octamethylcyclotetrasiloxane (D$_4$), was purchased from Gelest, Inc., Morrisville, Pa., and the reagent 1,3-bis(4-bromobutyl)tetramethyldisiloxane was purchased from Silar Laboratories (Scotia, N.Y.).

Analytical Methods

ESI-TOF MS: The electrospray (ESI) time of flight (TOF) MS analysis was performed on an Applied Biosystems Mariner instrument. The instrument operated in positive ion mode. The instrument was mass calibrated with a standard solution containing lysine, angiotensinogen, bradykinin (fragment 1-5) and des-Pro bradykinin. This mixture provides a seven-point calibration from 147 to 921 m/z. The applied voltage parameters were optimized from signal obtained from the same standard solution. For exact mass measurements poly (ethylene glycol) (PEG), having a nominal M$_n$ value of 400 Da, was added to the sample of interest and used as an internal mass standard. Two PEG oligomers that bracketed the sample mass of interest were used to calibrate the mass scale. Samples were prepared as 30 μM solutions in isopropanol (IPA) with the addition of 2% by volume saturated NaCl in IPA. Samples were directly infused into the ESI-TOF MS instrument at a rate of 35 µL/min. A sufficient resolving power (6000 RP m/Δm FWHM) was achieved in the analysis to obtain the monoistopic mass for each sample. In each analysis the experimental monoisotopic mass was compared to the theoretical monoisotopic mass as determined from the respective elemental compositions. In each analysis the monoisotopic mass comparison was less than 10 ppm error. It should be noted that uncharged samples have a sodium (Na) atom included in their elemental composition. This Na atom occurs as a necessary charge agent added in the sample preparation procedure. Some samples do not require an added charge agent since they contain a charge from the quaternary nitrogen inherent to their respective structure.

NMR: $^1$H-NMR characterization was carried out using a 400 MHz Varian spectrometer using standard techniques in the art. Samples were dissolved in chloroform-d (99.8 atom % D), unless otherwise noted. Chemical shifts were determined by assigning the residual chloroform peak at 7.25 ppm. Peak areas and proton ratios were determined by integration of baseline separated peaks. Splitting patterns (s=singlet, d=doublet, t=triplet, q=quartet, m=multiplet, br=broad) and coupling constants (J/Hz) are reported when present and clearly distinguishable.

SEC: Size Exclusion Chromatography (SEC) analyses were carried out by injection of 100 µL of sample dissolved in tetrahydrofuran (THF) (5-20 mg/mL) onto a Polymer Labs PL Gel Mixed Bed E (×2) column at 35° C. using a Waters 515 HPLC pump and HPLC grade THF mobile phase flow rate of 1.0 mL/min, and detected by a Waters 410 Differential Refractometer at 35° C. Values of $M_n$, $M_w$, and polydispersity (PD) were determined by comparison to Polymer Lab Polystyrene narrow standards.

Preparation

Step 1: Ring-Opening Polymerization. A solution of 1,3-bis(4-bromobutyl)tetramethyldisiloxane and octamethylcyclotetrasiloxane in a flask equipped with a stir bar and drying column was treated with trifluoroacetic acid and stirred 24 h at ambient T. To the reaction was added NaHCO$_3$ and the mixture was allowed to stir an additional 24 h at ambient T. The mixture was then filtered with pressure through a 5 µm PTFE filter, then stripped 2 h at 80° C. and 1-5 Torr to afford the product as a transparent, colorless, viscous liquid.

Step 2: Quaternization. The colorless liquid product from step 1 was then dissolved in ethyl acetate and treated with 2-(dimethylamino)ethyl methacrylate in a round bottomed flask equipped with magnetic stir bar. The reaction vessel was sealed in a manner to withstand the slight headspace pressure during subsequent heating. The reaction was then heated 100 h at 60° C. and in the dark. (NOTE: Due to the presence of polymerizable moiety, the reaction must be carefully monitored and controlled to avoid gelation, e.g. using a jacketed round bottom, oil bath, etc.). The cooled solution was then concentrated under reduced pressure (approximately 25 Torr and 40° C.). The resulting product mixture, ranging from viscous liquid to partial solid and clear to amber in color, was stripped at high vacuum (<1 Torr) and 60° C. to remove residual ethyl acetate and N,N-dimethylamino(ethyl methacrylate). Due to partial solidification during the stripping, frequent stirring/scraping/crushing of the product mixture, especially toward the end of stripping and especially for M$_2$D$_{14}$plus-B, may be required. The stripping is complete when no more residual monomer is being collected, and should not exceed 8 h. The resulting waxy solid product, ranging from colorless to light amber in color is then stored in amber vials at low temperature.

What is claimed is:

1. A monomer of formula (I):

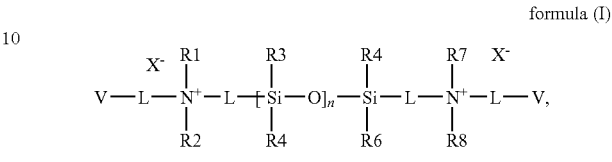

formula (I)

wherein L can be the same or different and is selected from the group consisting of urethanes, carbonates, carbamates, carboxyl ureidos, sulfonyls, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, a C5-C30 fluoroaryl group, or a hydroxyl substituted alkyl ether and combinations thereof; X$^-$ is at least a single charged counter ion; n is an integer from 1 to about 300; R1, R2, R3, R4, R5, R6, R7 and R8 are independently hydrogen, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, fluorine, a C5-C30 fluoroaryl group, or a hydroxyl group; and V is independently a free radical polymerizable ethylenically unsaturated organic radical.

2. The monomer of claim 1 wherein X$^-$ is selected from the group consisting of Cl$^-$, Br$^-$, I$^-$, CF$_3$CO$_2^-$, CH$_3$CO$_2^-$, HCO$_3^-$, CH$_3$SO$_4^-$, p-toluenesulfonate, HSO$_4^-$, H$_2$PO$_4^-$, NO$_3^-$, CH$_3$CH(OH)CO$_2^-$, SO$_4^{2-}$, CO$_3^{2-}$, HPO$_4^{2-}$ and mixtures thereof.

3. The monomer of claim 1 wherein X$^-$ is at least a single charged counter ion and is selected from the group consisting of Cl$^-$, Br$^-$, I$^-$, CF$_3$CO$_2^-$, CH$_3$CO$_2^-$, HCO$_3^-$, CH$_3$SO$_4^-$, p-toluenesulfonate, HSO$_4^-$, H$_2$PO$_4^-$, NO$_3^-$, and CH$_3$CH(OH)CO$_2^-$ and mixtures thereof.

4. The monomer of claim 1 wherein the monomer is selected from the group consisting of monomers having the following formulae:

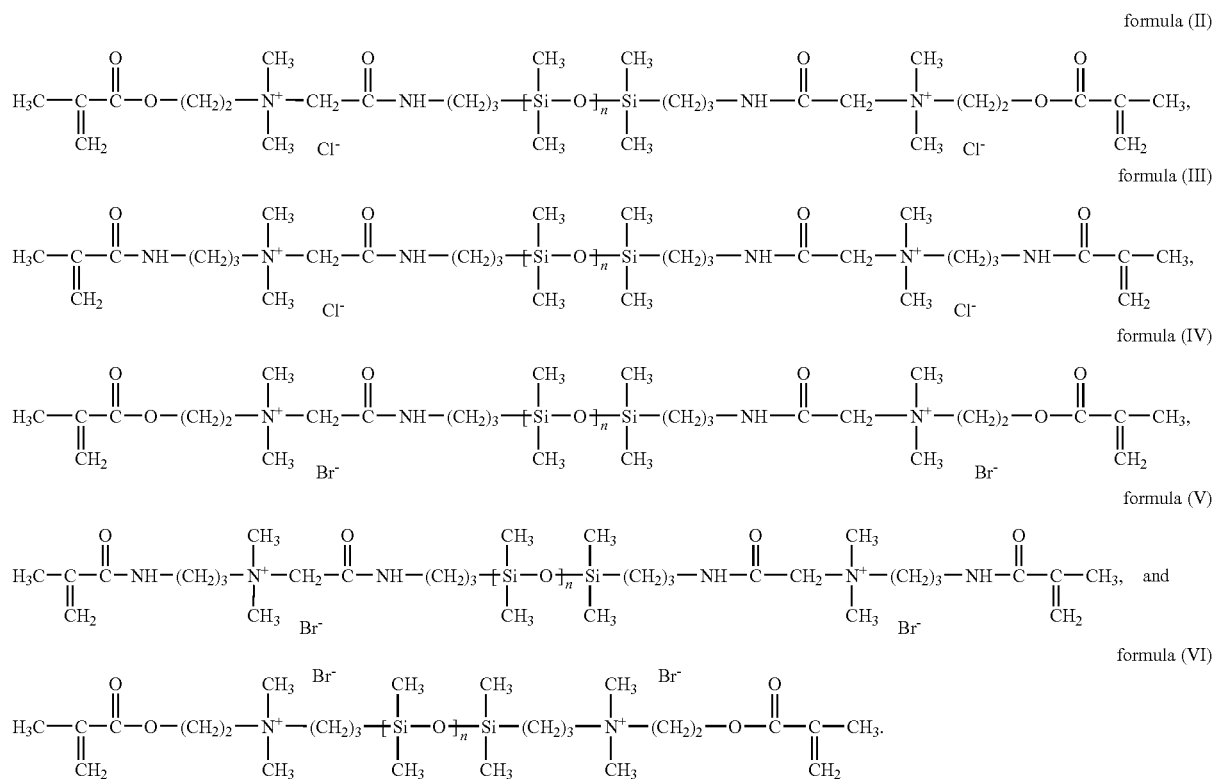

5. A monomer mix useful for making polymerized biomaterials comprising at least one monomer of claim 1 and at least one second monomer.

6. The monomer mix of claim 5, further comprising in addition to the second monomer a hydrophobic monomer and a hydrophilic monomer.

7. The monomer mix of claim 5 wherein the second monomer is selected from the group consisting of unsaturated carboxylic acids, acrylic substituted alcohols, vinyl lactams, acrylamides, methacrylates, hydrophilic vinyl carbonates, hydrophilic vinyl carbamate monomers, hydrophilic oxazolone monomers, and mixtures thereof.

8. A device comprising the monomer of claim 1 as a polymerized comonomer.

9. The device of claim 8 wherein the device is a contact lens.

10. The device of claim 9 wherein the contact lens is a rigid gas permeable contact lens.

11. The device of claim 9 wherein the contact lens is a soft contact lens.

12. The device of claim 9 wherein the contact lens is a hydrogel contact lens.

13. The device of claim 8 wherein the device is an intraocular lens.

14. The device of claim 13 wherein the intraocular lens is a phakic intraocular lens.

15. The device of claim 13 wherein the intraocular lens is an aphakic intraocular lens.

16. The device of claim 8 wherein the device is a corneal implant.

17. The device of claim 8 wherein the device is selected from the group consisting of heart valves, intraocular lenses, films, surgical devices, vessel substitutes, intrauterine devices, membranes, diaphragms, surgical implants, blood vessels, artificial ureters, artificial breast tissue, membranes for kidney dialysis machines, membranes for heart/lung machines, catheters, mouth guards, denture liners, ophthalmic devices, and contact lenses.

18. A method of making a device comprising:
providing a monomer mixture comprising the monomer of claim 1 and at least a second monomer;
subjecting the monomer mixture to polymerizing conditions to provide a polymerized device; and
extracting the polymerized device.

19. The method of claim 18 wherein the step of extracting is performed with non-flammable solvents.

20. The method of claim 18 wherein the step of extracting is performed with water.

21. A silicon containing monomer end-capped with free radical polymerizable ethylenically unsaturated cationic hydrophilic groups.

22. The monomer mix of claim 5 wherein the second monomer is methacryloxypropyl tris(trimethylsiloxy)silane.

23. The monomer mix of claim 22 further comprising 1-vinyl-2 pyrolidone, 2-hydroxyethyl methacrylate and 2,2'-azobis (2-methylpropionitrile).

24. The monomer mix of claim 23 further comprising N,N-dimethylacrylacide.

25. The monomer mix of claim 23 further comprising 1,3-Propanediol.

26. A device comprising the polymerized monomer mix of claim 24.

27. A device comprising the polymerized monomer mix of claim 25.

28. The monomer mix of claim 5 wherein the second monomer is selected from the group consisting of methacrylic acid, acrylic acid, 2-hydroxyethylmethacrylate, 2-hydroxyethylacrylate, N-vinylpyrrolidone, N-vinylcaprolactone, methacrylamide, N,N-dimethylacrylamide, ethylene glycol dimethylacrylate, methyl methacrylate, allyl methacrylate, methacryloxypropyltris(trimethylsiloxy)silane and mixtures thereof.

29. The method of claim 18 further comprising the step of packaging and sterilizing the polymerized device.

30. A biomedical device that is a polymerization product of a monomer mixture comprising the silicon containing monomer of claim 21.

31. The biomedical device of claim 30, wherein the monomer mixture further comprises a hydrophobic monomer, a hydrophilic monomer or both.

32. The biomedical device of claim 30, wherein the monomer mixture further comprises a second monomer selected from the group consisting of unsaturated carboxylic acids, acrylic substituted alcohols, vinyl lactams, acrylamides, methacrylates, hydrophilic vinyl carbonates, hydrophilic vinyl carbamate monomers, hydrophilic oxazolone monomers, and mixtures thereof.

33. The biomedical device of claim 30, wherein the device is a contact lens.

34. The biomedical device of claim 33, wherein the contact lens is a rigid gas permeable contact lens.

35. The biomedical device of claim 33, wherein the contact lens is a soft contact lens.

36. The biomedical device of claim 30, wherein the device is an intraocular lens.

37. The biomedical device of claim 30, wherein the device is a corneal implant.

* * * * *